United States Patent [19]

Kitamura et al.

[11] 4,313,934

[45] Feb. 2, 1982

[54] PHYSIOLOGICALLY ACTIVE POLYSACCHARIDES, PRODUCTION AND USES THEREOF

[75] Inventors: Kumpei Kitamura; Shigeru Matsuki; Kozo Tanabe, all of Takasaki, Japan

[73] Assignee: Kirin Beer Kabushiki Kaisha, Tokyo, Japan

[21] Appl. No.: 141,232

[22] Filed: Apr. 17, 1980

[30] Foreign Application Priority Data

May 8, 1979 [JP] Japan .................................. 54-55873
May 8, 1979 [JP] Japan .................................. 54-55874

[51] Int. Cl.³ .................... A61K 39/00; A61K 37/00; C07G 7/00
[52] U.S. Cl. ...................................... 424/85; 424/177; 260/112 R
[58] Field of Search ............... 260/112 R, 112.5 R; 424/85, 177

[56] References Cited

U.S. PATENT DOCUMENTS

| | | | |
|---|---|---|---|
| 4,094,971 | 6/1978 | Chedid et al. | 260/112.5 R |
| 4,110,434 | 8/1978 | Jolles et al. | 260/112.5 R |
| 4,153,686 | 5/1979 | Nagel | 260/112 R |
| 4,154,821 | 5/1979 | Drouet et al. | 260/112 R |

OTHER PUBLICATIONS

39519A/22, Ebiosu Yakuhin Kogy (EB10–) B04 D16.
30851T/19, Rikagaku Kenkyusho (Inst. (Rika) B04 D16.

*Primary Examiner*—Delbert R. Phillips
*Attorney, Agent, or Firm*—Ladas & Parry

[57] ABSTRACT

A physiologically active polysaccharide is prepared by treating autolysis-insoluble matters of yeasts of Saccharomyces with a yeast cell wall-lytic enzyme and obtaining a water-soluble physiologically active substance in the resulting solution-fraction. The novel polysaccharide possesses specific physical and chemical properties, and provides a chemotherapeutic agent such as a carcinostatic agent which can be used in the treatment of implanted tumors in mice and rats and an interferon inducer.

16 Claims, 5 Drawing Figures

—— : PRESENT INVENTION
--- : CONTROL
F I G. 3 (1)
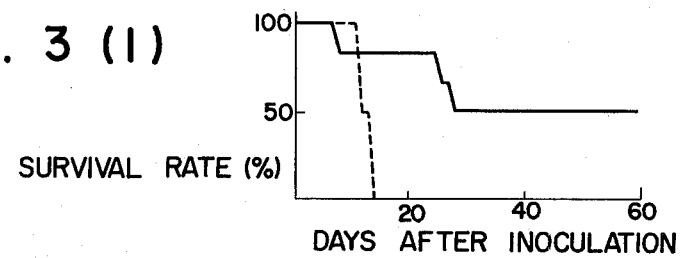
F I G. 3 (2)
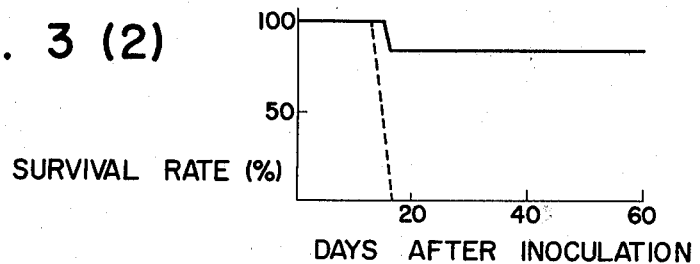
F I G. 3 (3)
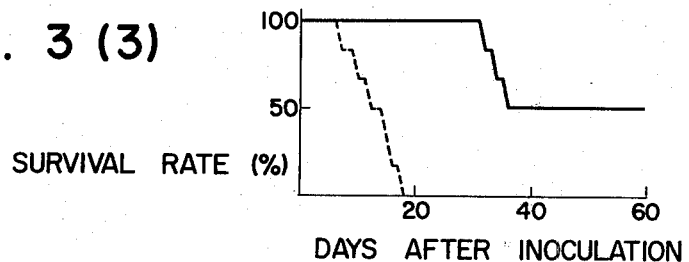

PHYSIOLOGICALLY ACTIVE POLYSACCHARIDES, PRODUCTION AND USES THEREOF

BACKGROUND OF THE INVENTION

1. Technical Field

This invention relates to a physiologically active substance, which is water-soluble derived from yeast cell walls, to its production and to a chemotherapeutic agent such as a carcinostatic or antitumor agent and an interferon inducer.

2. Prior Art

A number of the processes for production of carcinostatic substances from yeast cells have been known, most of which comprise subjecting yeast cells to hot water treatment, alkali treatment or autolysis treatment and obtaining water-soluble carcinostatic substances from the solution fractions. These processes, however, have low degree of utilization of yeast cells, and are also accompanied by problems such as that of waste water, which are not negligible.

The processes for obtaining carcinostatic substances from yeast cell walls themselves are described, for example, in Japanese Patent Publication No. 15712/1972 and Japanese Laid-open Patent Publication No. 44614/1978. The former invention comprises subjecting a specified yeast to treatments consisting essentially of autolysis, enzymatic treatment and warm weak-alkaline treatment, collecting the resulting cell wall fraction, and subjecting the fraction to strong-alkaline treatment under heat. The latter invention comprises using as an antitumor agent a water-insoluble fraction which has been obtained by removing a water-soluble extract from the autolysis product from brewer's yeasts. The latter carcinostatic substance is, of course, water-insoluble. The carcinostatic substance obtained by the former process is described as being water-soluble and being a carcinostatic high-molecular polysaccharide consisting of only glucose. The substance, however, is gelled in neutral water or an acidic water, and the gelled substance is soluble in an alkaline water (cf. Col. 3, lines 33 through 36 of the Publication).

The carcinostatic activities of these carcinostatic substances derived from yeast cells are described only for the case on Sarcoma 180 solid tumor of mice where the substances are administered intraperitoneally to the mice. The details of the effects on other tumors and/or other routes of administration of the substances are not clear.

SUMMARY OF THE INVENTION

It is an object of the present invention to provide a novel water-soluble physiologically active substance having a physiological activity such as carcinostatic activity which is derived from yeast cell walls. The physiologically active substance, which is a polysaccharide, is preferably prepared by treating enzymatically the insoluble fraction of yeast-autolysis products.

Thus, in one aspect of the present invention, there is provided a physiologically active polysaccharide which is derived from brewer's yeast cell walls and possesses the following physical and chemical properties:

(1) Elemental Analysis

| | |
|---|---|
| C | 40.9% ± 1.2% |
| H | 6.0% ± 0.2% |
| N | 1.9% ± 0.1% |
| O | 50.7% ± 1.5% |
| Ash | 0.5% ± 0.05% |

(2) Molecular Weight

An average molecular weight determined by ultrafiltration method is 140,000 to 220,000.

(3) Melting Point (Decomposition Point)

No melting point is generally observed in polysaccharides. The active polysaccharide turns brown at about 265° C. and black at about 270° C.

(4) Specific Rotation $[\alpha]_D^{25} = +75.0$ to $+55.0$ (C=1.0)

(5) Ultraviolet Absorption Spectra

The spectrum is as shown in FIG. 1. No specific absorption is observed therein.

(6) Infrared Absorption Spectra

The spectrum is as shown in FIG. 2.

(7) Solubility in Solvents

Soluble in water. Insoluble in methanol, ethanol, ether and acetone.

(8) Color Reaction

Positive in anthrone reaction, Molisch's reaction, ninhydrin reaction, biuret reaction and xanthoproteic reaction.

(9) Acidity

The pH of 1% aqueous solution thereof is 5.5 to 6.5.

(10) Color of the Polysaccharide

White.

(11) Constituent Sugars and Compositions thereof 75 to 86% of mannose, 14 to 25% of glucose; and a small quantity of glucosamine is detected.

(12) Bond-structure of the Sugar

Mannose is linked by α-bond since a sugar is liberated therefrom by an α-mannanase.

(13) Constituent Amino Acids and Compositions thereof 26 to 32% of serine, 16 to 20% of threonine, 13 to 17% of alanine, 7 to 9% of proline, 5 to 7% of glutamic acid, 5 to 7% of aspartic acid, 4 to 6% of valine, 3 to 5% of lysine, 3 to 4% of glycine, 2.5 to 3.5% of isoleucine, 1.5 to 2.5% of leucine, 0.5 to 1.5% of tyrosine, and 0.3 to 0.7% of phenylalanine.

In another aspect of the present invention, there is also provided a chemotherapeutic agent which is a carcinostatic agent or an interferon inducer.

Moreover, in accordance with another aspect of the present invention, there is provided a process for preparation of physiologically active polysaccharides, which comprises treating an insoluble matter of autolysis of yeast of Saccharomyces with a yeast cell wall-lytic enzyme, and obtaining a water-soluble physiologically active substance in the resulting solution-fraction.

The water-soluble physiologically active substance is produced from the yeast cell walls of Saccharomyces which have been subjected to autolysis to form insoluble matters. This substance consists essentially of mannose.

It has been found that this novel polysaccharide has a carcinostatic action on the Sarcoma 180 solid tumor grown on mice when administered intraperitoneally as well as some other tumors. This substance is considered to exhibit its carcinostatic action on the immunity system of cancer-bearing animals, and the carcinostatic action is observed also when administered per os, which is very advantageous in its actual use. It has also been observed that this substance has a carcinostatic action on the ascites hepatoma AH 130 of rats. This tumor, however, has been generally known to be not combated by a carcinostatic agent which promotes immunity system. Thus, it is considered that there is a significant difference in the mode of action between the present substance and the conventionally known carcinostatic polysaccharides.

In accordance with the present invention, the novel polysaccharide is obtained by utilizing the by-product of the process for preparation of yeast extracts since the residues after extraction of yeast extracts by the autolysis method can be used as a raw material, and the process of the present invention for preparation of the substance itself is also simple.

BRIEF DESCRIPTION OF THE DRAWINGS

In the drawings:

FIGS. 3(1), (2) and (3) are graphs showing the effects of a physiologically active substance of the present invention on the ascites hepatoma of rats.

DETAILED DESCRIPTION OF THE INVENTION

Figure 1:
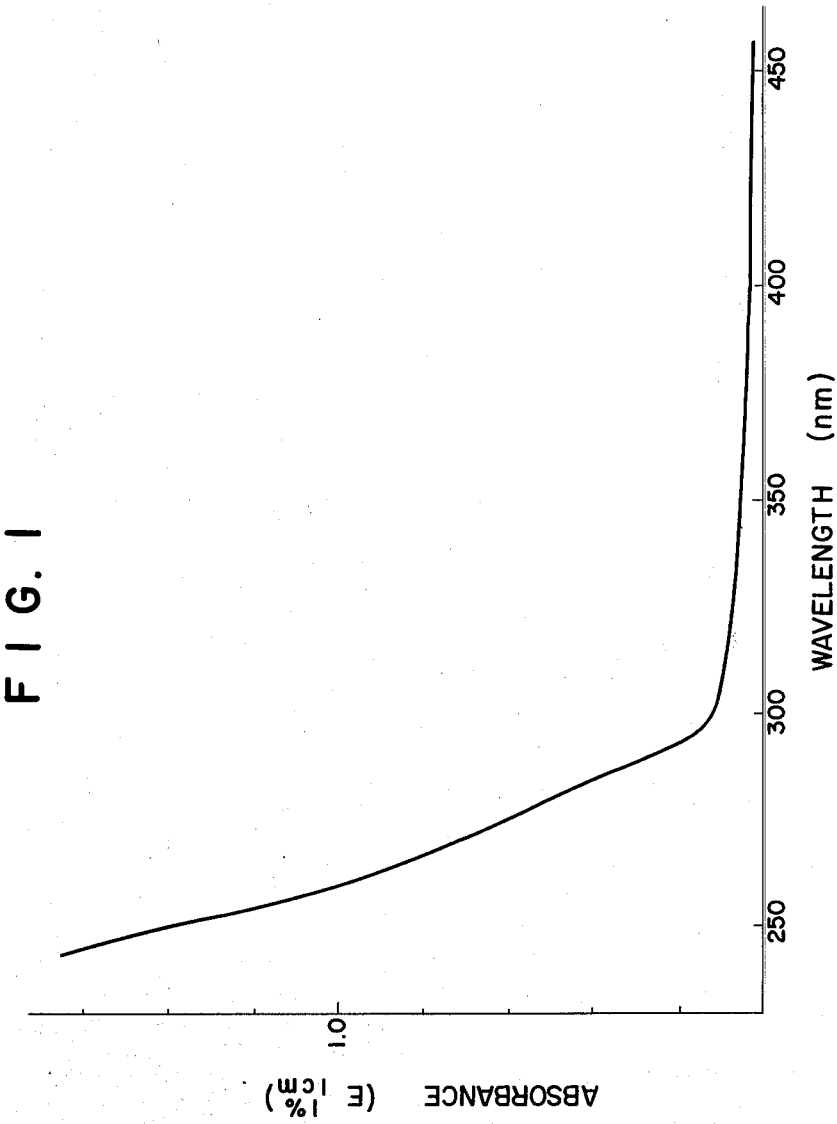
FIGS. 1 and 2 are respectively copies of an ultraviolet absorption spectrogram and an infrared absorption spectrogram of a physiologically active substance of the present invention.

1. Autolysis-Insoluble Matters of Yeast The autolysis process, the insoluble matters and the process for recovery thereof are substantially the same as those in conventional practice except that the yeasts are of Saccharomyces.

The yeasts of Saccharomyces include, for example, brewer's yeast, Japanese sake yeasts, baker's yeasts and the like.

Typical yeasts used in the present invention are brewer's yeasts and baker's yeasts. The specific yeast strains include S. cerevisiae, S. carlsbergensis, and the like.

Autolysis of yeasts can be carried out according to the methods for production of conventional yeast extracts. More specifically, for example, the yeast is suspended in water or a suitable aqueous solvent, to which a small amount of an organic solvent such as toluene is added, and then the mixture is subjected to autolysis at 30° to 50° C. for 30 to 60 hours. The resulting autolytic reaction product is subjected to a separation process such as centrifuging to obtain autolysis-insoluble matters.

The autolysis-insoluble matters suitable for use in the present invention are the residues remaining after extraction of yeast extracts which have been produced as a by-product in the process for autolytic production of yeast extracts from yeasts and preferably from brewer's yeasts.

2. Treatment with Enzymes (1) Yeast cell wall-lytic enzymes

The yeast cell wall-lytic enzymes for use in the present process are represented by the enzymes which are produced by bacteria of Arthrobacter, preferably A. luteus nov. sp. ATCC 21606, (cf. Japanese Patent Publication Nos. 32674/1972 and 2790/1973, U.S. Pat. No. 3,716,452, British Pat. No. 1,281,618, or British Pat. No. 2,085,426), and the enzymes which bacteria of Oerskovia produce (cf. J. Bacteriol, Vol. 111, page 821, 1972). Other yeast cell wall-lytic enzymes similar to those enzymes can also be used if desired. Preferably these enzymes should have been purified at least in part.

A specific example of these enzymes is commercially available "ZYMOLYASE" (trade name registered in Japan), which is an enzyme produced by Arthrobacter, such as Zymolyase 60000.

(2) Enzymatic Reaction

A suitable quantity (e.g., 15 to 200 units and preferably 30 to 80 units per gram of the autolysis-insoluble matters) of the enzyme is added to a suspension containing the autolysis-insoluble autolysis matters in a suitable concentration thereof (e.g., 5 to 30%). The mixture is subjected to reaction with stirring for a suitable time (e.g., 0.5 to 6 hours) at a suitable pH (e.g., pH of 6.0 to 9.0 and preferably 7.0 to 8.0) and at a suitable temperature (e.g., 20° to 50° C. and preferably 35° to 45° C.). The yield of the present carcinostatic substance can be increased by subjecting in advance the starting autolysis-insoluble matters to stirring at room temperature for 5 to 60 minutes in an alkaline aqueous solution of not lower than about pH 12. During the treatment, a sulfite (e.g., sodium sulfite or potassium sulfite) or an SH group-containing compound (e.g., mercaptoethanol) known as a promotor of the action of the yeast cell wall-lytic enzymes can be present in the alkali treatment. These sulphur-containing compounds can also be present in the reaction mixture of the above-described enzymatic treatment. Incidentally, the above-mentioned unit of enzyme is fully described in Japanese Patent Publication No. 32674/1972 and is defined as follows.

One unit of lytic activity is defined as that amount which indicates 30% of decrease in optical density at 800 nm ($OD_{800}$) of the reaction mixture under the following condition:

A mixture of 1 ml of enzyme solution, 3 ml of brewer's yeast cell suspension (2 mg dry weight/ml), 5 ml of M/15 phosphate buffer (pH 7.5), and 1 ml of water, is incubated at 25° C. for 2 hours with gentle shaking, and then $OD_{800}$ of the mixture is determined. As a reference, 1 ml of water is used instead of enzyme solution. Percentage decrease in $OD_{800} = (OD_{800}$ of reference $- OD_{800}$ of reaction mixture$) \times 100/$initial $OD_{800}$ of reference.

After the reaction for a predetermined time, the pH of the reaction mixture is adjusted to a pH of about 3.0 to 6.0 and preferably about 3.5 to 4.5, and then insoluble matters are removed by centrifuging or like process to obtain a transparent solution. Before recovery of the present carcinostatic substance from the solution, the solution is normally subjected to a deproteinization treatment in accordance with a conventional method. The deproteinization treatment comprises, for example, adding and dissolving trichloroacetic acid as a suitable protein-precipitant in an amount such that its concentration will be about 2 to 4% into the above-mentioned solution, leaving the mixture to stand at a low temperature (e.g., not higher than 5° C.) for about 2 hours or more, and then removing the resulting precipitate by centrifuging, filtration, or like process.

A water-miscible, organic non-solvent such as methanol or ethanol is added to the resulting solution to precipitate the present physiologically active substance. The resulting precipitate is collected and dissolved in water, and the above-mentioned water-miscible organic non-solvent is added thereto to precipitate the substance again. This dissolution-precipitation treatment can be carried out once to several times, in which it is preferred that at least one treatment be conducted under an alkaline condition of pH 11.0 or higher as shown in the working examples. The substance is further subjected to a dialysis treatment against water to remove low molecular fractions. Thus, there is obtained the present physiologically active substance in the form of an aqueous solution. The solution is freeze-dried to obtain the present physiologically active substance as a solid preparation. The present substance may be further purified if desired by a conventional method such as the gel-filtration method or the ion-exchange method.

3. Physiologically Active Substance

The present physiologically active substance thus obtained is estimated to be a protein-polysaccharide which contains mannose as a major component and comprises 70 to 90% of carbohydrates and 0.5 to 3.0% of nitrogen. The substance is soluble in water, insoluble in such an organic solvent as methanol, ethanol and acetone, and exhibits a positive color reaction in anthrone reaction, Molisch's reaction, ninhydrin reaction or biuret reaction. It is readily appreciated that the precise physical and chemical properties of the present substance differ from each other on the basis of the type of yeasts, the type of yeast cell wall-lytic enzymes, and the method and degree of purification. In any case, however, the present substance exhibits marked carcinostatic action.

The physical and chemical properties and physiological action of the samples of the present substance obtained in the examples described hereinafter are as follows.

(1) Physical and Chemical Properties
(1) Elemental Analysis

| | |
|---|---|
| C | 40.9% ± 1.2% |
| H | 6.0% ± 0.2% |
| N | 1.9% ± 0.1% |
| O | 50.7% ± 1.5% |
| Ash | 0.5% ± 0.05% |

(2) Molecular Weight

An average molecular weight determined by the ultrafiltration method is 140,000 to 220,000.

(3) Melting Point (Decomposition Point)

No melting point is generally observed in polysaccharides. The active polysaccharide turns brown at about 265° C. and black at about 270° C.

(4) Specific Rotation $[\alpha]_D^{25} = +75.0$ to $+55.0$ (C=1.0)

(5) Ultraviolet Absorption Spectra

The spectrum is as shown in FIG. 1. No specific absorption is observed therein.

(6) Infrared Absorption Spectra

Figure 2:
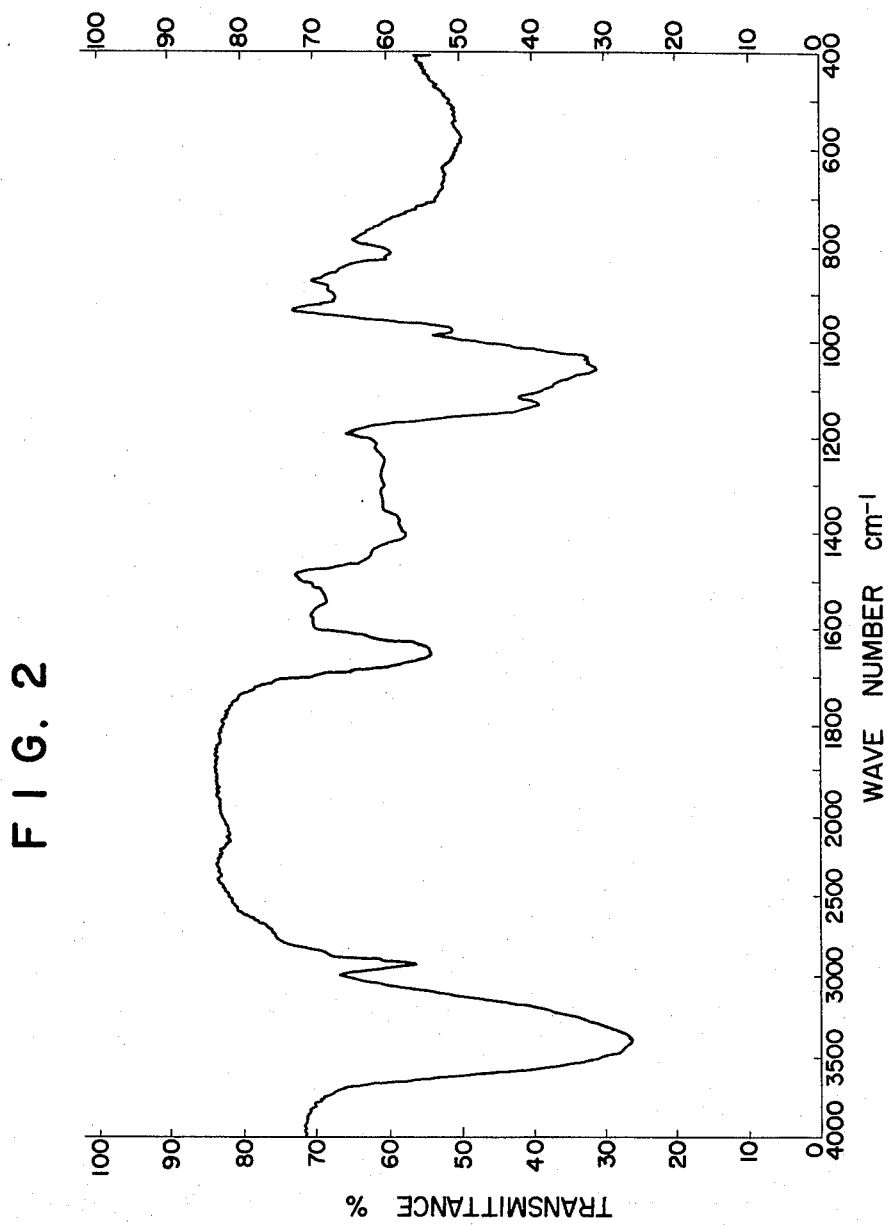

The spectrum is as shown in FIG. 2.

(7) Solubility in Solvents

Soluble in water. Insoluble in methanol, ethanol, ether and acetone.

(8) Color Reaction

Positive in anthrone reaction, Molisch's reaction, ninhydrin reaction, biuret reaction and xanthoproteic reaction.

(9) Acidity

The pH of 1% aqueous solution thereof is 5.5 to 6.5.

(10) Color of the polysaccharide

White.

(11) Constituent Sugars and Compositions thereof 75 to 86% of mannose, 14 to 25% of glucose; and a small quantity of glucosamine is detected.

(12) Bond-structure of the Sugar

Mannose is linked by $\alpha$-bond since a sugar is liberated therefrom by an $\alpha$-mannanase.

(13) Constituent Amino Acids and Compositions thereof 26 to 32% of serine, 16 to 20% of threonine, 13 to 17% of alanine, 7 to 9% of proline, 5 to 7% of glutamic acid, 5 to 7% of aspartic acid, 4 to 6% of valine, 3 to 5% of lysine, 3 to 4% of glycine, 2.5 to 3.5% of isoleucine, 1.5 to 2.5% of leucine, 0.5 to 1.5% of tyrosine, and 0.3 to 0.7% of phenylalanine.

(2) Physiological Activity

The physiological activity is as follows.

(1) Carcinostatic Action (a) Action on Sarcoma 180 of Mice

Male ddY mice 5 weeks old were inoculated subcutaneously with 5,000,000 cells of Sarcoma 180 cells in the right groin of mice. From the next day on, the present substance was administered 10 times once a day to the inoculated mice with the routes of administration and at the dosages shown in Table 1. Five weeks after the inoculation, the mice were sacrificed and the tumors were removed. The removed tumors were weighed and compared with those of control groups to calculate percent inhibition. The results are shown in Table 1. For comparison, the commercially available carcinostatic agent derived from *Coriolus versicolor* was tested under the same conditions.

TABLE 1

| Carcinostatic substance | Routes of administration | Dosage (mg/kg) | Percent inhibition (%) |
|---|---|---|---|
| The present substance | intraperitoneally | 10 | 74 |
| | orally | 250 | 52 |
| Commerically available substance | intraperitoneally | 10 | 37 |
| | orally | 250 | 40 |

The present substance when administered either intraperitoneally or orally exhibited a carcinostatic action superior to that of the commercially available substance.

(b) Action on Ascites Hepatoma of Rats

As tumor cells, AH130, AH66 and AH44 were used. Male Donryu rats (about 150 g) were employed as test animals. About 10,000,000 cells of the tumor cells were inoculated into the tail veins of the rats. Three days after the inoculation of the tumor, the present substance dissolved in saline was administered in a daily dosage of 100 mg/kg once a day for 10 days. The percent survival of the rats were observed for 60 days after the inoculation to obtain the results shown in FIGS. 3(1), (2), and (3). FIG. 3(1), FIG. 3(2) and FIG. 3(3) show the antitumor effects against ascitic AH130, ascitic AH66, and ascitic AH44, respectively, tumor cells in rats. The curves of solid lines show the cases of the groups administered with the present substance. The curves of dotted lines show the cases of the control groups administered with saline only.

None of the control groups survived 20 days. The groups administered with the present substance were surviving on the 60th days after the inoculation with the percent survival of 50% in the case of AH130 or AH44 and that of 83% in the case of AH66. The commercially available carcinostatic agent derived from *Coriolus versicolor* was also tested under the same conditions. The difference in percent survival was not observed between the groups administered with the substance and the control groups.

(c) Interferon-inducing Action

The present substance was administered intraperitoneally in a dosage of 100 mg/kg to male C3H mice 7 weeks old. The blood was collected from each mouse 24 hours after the administration to determine an interferon titer of the serum thereof. The interferon titer induced in 1 ml of the serum was 800 international units. The commercially available carcinostatic agent derived from *Coriolus versicolor* was tested under the same conditions to determine its interferon-inducing action. The interferon titer induced thereby in 1 ml of the serum was 200 international units or lower.

(3) Dosage Form

A chemotherapeutic agent such as a carcinostatic agent and interferon inducer which contains the abovementioned physiological active substance as the effective component may be of any reasonable dosage form. The chemotherapeutic agent comprises a pharmacologically effective amount of the active component and a pharmacologically-acceptable carrier.

When the substance is in powder form, forms of powder, tablets with suitable excipients and the like are suitable.

Since the substance is water-soluble, it can be in the form of a liquid medicine dissolved in water.

The chemotherapeutic agent can be administered, depending on its dosage form, by oral administration, injection, rectal administration or other appropriate mode of administration.

(4) Dosage

The specific dosage should be determined by a physician in consideration of the conditions and states of the patients and the like. In general, the dosage is about 20 to 200 mg/kg body weight per day.

(5) Toxicity

Acute toxicity in mice was tested as follows.

In this test dd mice 5 weeks old having body weights of 20 to 27 grams were employed. The present substance was administered orally or intraperitoneally. The survival or death and symptoms of the mice were observed for 7 days after the administration of the present substance. As a result, even at the maximum dosage which can be administered technically, no case of death was observed. The $LD_{50}$ in either oral or intraperitoneal administration was estimated to be 5,000 mg/kg or more.

4. Experiments

In the following examples, Zymolyase 60000 (trade name) was used as the yeast cell wall-lytic enzyme. As the starting material, the residue as a by-product in the production of yeast extracts by autolysis of brewer's yeast supplied from Kirin Brewery Co., Ltd., Japan, was used.

EXAMPLE 1

Two hundred (200) grams of the starting material was suspended in water to make a 2-liter suspension, into which 25.6 g of sodium sulfite was added and dissolved. The mixture was adjusted to a pH of 8.0, and 200 mg of the enzyme was added thereto. Reaction was carried out with stirring at 38° C. for 3 hours. After termination of the reaction, the reaction mixture was adjusted with hydrochloric acid to a pH of 4.0 and was then subjected to centrifuging to obtain a supernatant. Trichloroacetic acid in the amount of 2.5% of the resulting mixture was added to the supernatant. The mixture was allowed to stand at 2° C. overnight.

The separated precipitates were removed by centrifuging. To the liquid was added a 2-fold amount of ethanol to form precipitates. The precipitates were collected and redissolved in water, and 2-fold amount of ethanol was added again thereto to form precipitates. The resulting precipitates were collected and dissolved in water. The solution was adjusted with a sodium hydroxide solution to a pH of 12, and then to this solution was added a 2-fold amount of ethanol to form precipitates. The precipitates were collected and dissolved again in water.

The resulting solution was adjusted to neutral pH and then subjected to dialysis against running tap water, which was followed by dialysis against pure water for one day. Insoluble matters in the dialyzed inner liquid were removed by centrifuging, and the liquid was freezedried. The yield of the resulting physiologically active substance was 21.6 g.

EXAMPLE 2

Two hundred (200) grams of the starting material was suspended in water to make a 2-liter suspension. The suspension was adjusted with a sodium hydroxide solution to a pH of 13 and was then stirred at room temperature for 30 minutes. It was then adjusted with hydrochloric acid to a pH of 8.0, and 500 mg of the enzyme was added thereto. The resulting mixture was reacted with stirring at 38° C. for 3 hours. After termination of the reaction, 17.3 g of a physiologically active substance was obtained from the reaction mixture in the same way as in Example 1.

EXAMPLE 3

Two hundred (200) grams of the starting material was suspended in water. To the suspension was added 25.6 g of sodium sulfite, and then the suspension was adjusted with a sodium hydroxide solution to a pH of 12.8, which step was followed by stirring at room temperature for 10 minutes. Adjustment was then made with hydrochloric acid to a pH of 8.0, and 500 mg of the enzyme was added to the process. Reaction was carried out with stirring at 38° C. for 3 hours. After termination of the reaction, 30.5 g of the physiologically active substance was obtained from the reaction mixture in the same way as in Example 1.

EXAMPLE 4

Forty (40) grams of the starting material was suspended in water to make a 400-ml suspension, which was adjusted with a sodium hydroxide solution to a pH of 8.0, and then 27 mg of the enzyme was added thereto. The mixture was subjected to reaction with stirring at 35° C. for 2 hours. After termination of the reaction, 4.3 g of the physiologically active substance was obtained from the reaction mixture in the same way as in Example 1.

Quantities expressed herein in percentages, ratios and the like are based on weight, unless otherwise specified.

What is claimed is:

1. A physiologically active polysaccharide which is derived from brewer's yeast cell walls and possesses:
   (1) an elemental analysis as follows by weight

| | |
   |---|---|
   | C | 40.9% ± 1.2% |
   | H | 6.0% ± 0.2% |
   | N | 1.9% ± 0.1% |
   | O | 50.7% ± 1.5% |
   | Ash | 0.5% ± 0.05%; |

(2) an average molecular weight determined by an ultrafiltration method of 140,000 to 220,000;
   (3) no melting point since no melting point is generally observed in polysaccharides, the active polysaccharide turning brown at about 265° C. and black at about 270° C.;
   (4) a specific rotation expressed by $[\alpha]_D^{25} = +75.0$ to $+55.0$ (C=1.0);
   (5) an ultraviolet absorption spectrum as shown in FIG. 1, in which no specific absorption is observed;
   (6) an infrared absorption spectrum as shown in FIG. 2;
   (7) solubility in water and insolubility in methanol, ethanol, ether and acetone;
   (8) a positive color reaction in anthrone reaction, Molisch's reaction, ninhydrin reaction, biuret reaction and xanthoproteic reaction;
   (9) a pH of a 1% aqueous solution thereof of 5.5 to 6.5; (10) a white color;
   (11) 75 to 86% of mannose and 14 to 25% of glucose, a small quantity of glucosamine being detected;
   (12) a bond structure of the sugar in which mannose is linked by α-bond since a sugar is liberated therefrom by an α-mannanase; and
   (13) constituent amino acids comprising 26 to 32% of serine, 16 to 20% of threonine, 13 to 17% of alanine, 7 to 9% of proline, 5 to 7% of glutamic acid, 5 to 7% of aspartic acid, 4 to 6% of valine, 3 to 5% of lysine, 3 to 4% of glycine, 2.5 to 3.5% of isoleucine, 1.5 to 2.5% of leucine, 0.5 to 1.5% of tyrosine, and 0.3 to 0.7% of phenylalanine.

2. A chemotherapeutic agent which can be used in the treatment of implanted tumors in mice and rats and which comprises an effective carcinostatic amount of the polysaccharide of claim 1 and a pharmacologically acceptable carrier.

3. A chemotherapeutic agent which can be used in the treatment of implanted tumors in mice and rats and which comprises the polysaccharide of claim 1 in an amount effective to increase an interferon titer and a pharmacologically acceptable carrier.

4. A process for preparation of a physiologically active polysaccharide, which comprises causing a yeast cell wall-lytic enzyme to act on an autolysis-insoluble matter of a yeast of Saccharomyces, and obtaining a water-soluble physiologically active polysaccharide in the resulting solution-fraction.

5. The process as set forth in claim 4, in which the yeast is selected from the group consisting of brewer's yeasts and baker's yeasts.

6. The process as set forth in claim 4, in which the yeast cell wall-lytic enzyme is an enzyme produced by a bacterium selected from the group consisting of the bacteria of Arthrobacter and Oerskovia.

7. The process as set forth in claim 6, in which the yeast cell wall-lytic enzyme is an enzyme produced by the bacteria of Arthrobacter.

8. The process as set forth in claim 7, in which the bacterium is that of Arthrobacter which is ATCC 21606 bacterium.

9. The process as set forth in claim 4, in which the process comprises adding 15 to 200 units of the enzyme per gram of the yeast-autolysis insoluble matter to a suspension containing 5 to 30% of the insoluble matter, and carrying out reaction at a pH of 6.0 to 9.0 and at a temperature of 20° to 50° C.

10. The process as set forth in claim 4, in which the yeast-autolysis insoluble matter has been contacted, at room temperature for 5 to 60 minutes, with an alkaline aqueous solution having a pH of 12 or higher.

11. The process as set forth in claim 4 which comprises, after termination of the enzymatic reaction, adjusting the pH of the reaction mixture to 3.0 to 6.0, removing any insoluble matters and obtaining a solution of the desired physiologically active polysaccharide.

12. The process as set forth in claim 11, in which a water-miscible organic non-solvent is added to the solution of the desired physiologically active polysaccharide to obtain the physiologically active polysaccharide as precipitates.

13. The process as set forth in claim 12, in which the resulting physiologically active polysaccharide is purified by subjecting the polysaccharide at least once to a purification treatment which comprises dissolving the polysaccharide in water and adding a water-miscible organic nonsolvent to the resulting solution to precipitate the polysaccharide.

14. The process as set forth in claim 13, in which at least one of the purification treatments is carried out under an alkaline condition of pH 11 or higher.

15. The process as set forth in claim 14, in which the resulting physiologically active polysaccharide possesses:
   (1) an elemental analysis as follows by weight

| | |
   |---|---|
   | C | 40.9% ± 1.2% |
   | H | 6.0% ± 0.2% |
   | N | 1.9% ± 0.1% |
   | O | 50.7% ± 1.5% |
   | Ash | 0.5% ± 0.05%; |

(2) an average molecular weight determined by an ultrafiltration method of 140,000 to 220,000;
   (3) no melting point since no melting point is generally observed in polysaccharides, the active polysaccharide turning brown at about 265° C. and black at about 270° C.;
   (4) a specific rotation expressed by $[\alpha]_D^{25} = +75.0$ to $+55.0$ (C=1.0);
   (5) an ultraviolet absorption spectrum as shown in FIG. 1, in which no specific absorption is observed;
   (6) an infrared absorption spectrum as shown in FIG. 2;
   (7) solubility in water and insolubility in methanol, ethanol, ether and acetone;
   (8) a positive color reaction in anthrone reaction, Molisch's reaction, ninhydrin reaction, biuret reaction and xanthoproteic reaction;
   (9) a pH of a 1% aqueous solution thereof of 5.5 to 6.5;
   (10) a white color;

(11) 75 to 86% of mannose and 14 to 25% of glucose, a small quantity of glucosamine being detected;
(12) a bond structure of the sugar in which mannose is linked by α-bond since a sugar is liberated therefrom by an α-mannanase; and
(13) constituent amino acids comprising 26 to 32% of serine, 16 to 20% of threonine, 13 to 17% of alanine, 7 to 9% of proline, 5 to 7% of glutamic acid, 5 to 7% of aspartic acid, 4 to 6% of valine, 3 to 5% of lysine, 3 to 4% of glycine, 2.5 to 3.5% of isoleucine, 1.5 to 2.5% of leucine, 0.5 to 1.5% of tyrosine, and 0.3 to 0.7% of phenylalanine.

16. A method for increasing the interferon titer of a patient comprising administering to said patient the polysaccharide of claim 1 in an amount effective to increase the interferon titer.

* * * * *